US00PP20574P2

(12) United States Plant Patent
Woods

(10) Patent No.: US PP20,574 P2
(45) Date of Patent: Dec. 15, 2009

(54) ***HIBISCUS* PLANT NAMED 'NOTWOOD3'**

(50) Latin Name: *Hibiscus syriacus*
Varietal Denomination: Notwood3

(75) Inventor: Roderick Woods, King's Lynn (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/228,275

(22) Filed: Aug. 11, 2008

(51) Int. Cl.
*A01H 5/00* (2006.01)

(52) U.S. Cl. ..... Plt./257

(58) Field of Classification Search ..... Plt./257

See application file for complete search history.

*Primary Examiner*—June Hwu
(74) *Attorney, Agent, or Firm*—C. A. Whealy

(57) ABSTRACT

A new and distinct cultivar of *Hibiscus* plant named 'Notwood3', characterized by its upright and somewhat outwardly spreading plant habit; vigorous growth habit; freely branching habit; large blue-colored flowers with numerous petaloids; and good garden performance.

2 Drawing Sheets

Botanical designation: *Hibiscus syriacus*.
Cultivar denomination: 'Notwood3'.

BACKGROUND OF THE INVENTION

The present invention relates to a new and distinct cultivar of *Hibiscus,* botanically known as *Hibiscus syriacus*, commercially known as Rose-of-Sharon or Althea, and hereinafter referred to by the name 'Notwood3'.

The new *Hibiscus* plant is a product of a planned breeding program conducted by the Inventor in Lynn, United Kingdom. The objective of the breeding program was to develop new *Hibiscus* cultivars with unique flower shapes and coloration, uniform plant habit and hardiness.

The new *Hibiscus* plant originated from a cross-pollination during the summer of 2001 of a proprietary seedling selection of *Hibiscus syriacus* identified as code number 219, not patented, as the female, or seed, parent with a proprietary seedling selection of *Hibiscus syriacus* identified as code number 202-717, not patented, as the male, or pollen, parent. The new *Hibiscus* plant was discovered and selected by the Inventor in August, 2003 as a flowering plant within the progeny of the stated cross-pollination in a controlled outdoor nursery environment in Lynn, United Kingdom.

Asexual reproduction of the new *Hibiscus* plant by softwood cuttings in a controlled greenhouse environment in Lynn, United Kingdom since the spring of 2004 has shown that the unique features of this new *Hibiscus* plant are stable and reproduced true to type in successive generations of asexual reproduction.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Notwood3'.

These characteristics in combination distinguish 'Notwood3' as a new and distinct cultivar of *Hibiscus*:

1. Upright and somewhat outwardly spreading plant habit.
2. Vigorous growth habit.
3. Freely branching habit.
4. Large blue-colored flowers with numerous petaloids.
5. Good garden performance.

Plants of the new *Hibiscus* can be compared to plants of the female parent selection. Plants of the new *Hibiscus* differ primarily from plants of the female parent selection in flower form as plants of the female parent selection do not have flowers with petaloids.

Plants of the new *Hibiscus* can be compared to plants of the male parent selection. Plants of the new *Hibiscus* differ primarily from plants of the male parent selection in flower size and color as plants of the male parent selection have smaller and lighter blue-colored flowers.

Plants of the new *Hibiscus* can be compared to plants of the *Hibiscus syriacus* 'Notwoodone', disclosed in U.S. Plant Pat. No. 12,619. In side-by-side comparisons conducted in Grand Haven, Mich., plants of the new *Hibiscus* differed from plants of 'Notwoodone' primarily in flower color as plants of 'Notwoodone' had lavender-colored flowers.

Plants of the new *Hibiscus* can also be compared to plants of the *Hibiscus syriacus* 'Notwoodtwo', disclosed in U.S. Plant Pat. No. 12,612. In side-by-side comparisons conducted in Grand Haven, Mich., plants of the new *Hibiscus* differed from plants of 'Notwoodtwo' primarily in flower color as plants of 'Notwoodtwo' had pure white-colored flowers.

BRIEF DESCRIPTION OF THE PHOTOGRAPHS

The accompanying colored photographs illustrate the overall appearance of the new *Hibiscus*, showing the colors as true as it is reasonably possible to obtain in colored reproductions of this type. Colors in the photographs may differ slightly from the color values cited in the detailed botanical description which accurately describe the colors of the new *Hibiscus*.

The photograph on the first sheet is a side perspective view of a typical plant of 'Notwood3' grown in a container in an outdoor nursery.

The photograph on the second sheet is a close-up view of a typical flower of 'Notwood3'.

DETAILED BOTANICAL DESCRIPTION

The aforementioned photographs and following observations, measurements and values describe plants grown in Grand Haven, Mich. during the summer in a polypropylene-covered shadehouse and under conditions which closely approximate commercial production. Plants were 2.5 years old when the photographs and the description were taken. In the description, color references are made to The Royal Horticultural Society Colour Chart, 1995 Edition, except where general terms of ordinary dictionary significance are used.

Botanical classification: *Hibiscus syriacus* 'Notwood3'.

Parentage:

*Female, or seed, parent.*—Proprietary seedling selection of *Hibiscus syriacus* identified as code number 219, not patented.

*Male, or pollen, parent.*—Proprietary seedling selection of *Hibiscus syriacus* identified as code number 202-717, not patented.

Propagation:

*Type.*—By softwood cuttings.

*Time to initiate roots.*—About three weeks at 27° C.

*Time to produce a rooted young plant.*—About four months at 27° C.

*Root description.*—Thick, somewhat fleshy.

*Rooting habit.*—Moderately freely branching.

Plant description:

*Plant form and growth habit.*—Perennial shrub. Compact, upright and somewhat outwardly spreading plant habit. Vigorous growth habit.

*Branching habit.*—Freely branching, usually about 36 lateral branches develop per plant after pinching (removal of terminal apices).

*Plant height.*—About 1.5 meters.

*Plant diameter* (*area of spread*).—About 1 meter.

Lateral branch description:

*Length.*—About 48 cm.

*Diameter.*—About 4 mm.

*Internode length.*—About 5.8 cm.

*Texture, immature.*—Smooth, glabrous.

*Texture, mature.*—Woody.

*Color, immature.*—Close to 137A.

*Color, mature.*—Close to 198A.

Foliage description:

*Arrangement.*—Alternate, simple.

*Length.*—About 7 cm.

*Width.*—About 4 cm.

*Shape.*—Ovate to rhomboid.

*Apex.*—Acute.

*Base.*—Cuneate.

*Margin.*—Crenate; lobed.

*Texture, upper and lower surfaces.*—Smooth, glabrous.

*Venation pattern.*—Palmate; reticulate.

*Color.*—Developing and fully expanded leaves, upper surface: Close to 146A; venation, close to 146B. Developing and fully expanded leaves, lower surface: Close to 146B; venation, close to 146B.

*Petiole.*—Length: About 1.2 cm. Diameter: About 1.5 mm. Texture, upper and lower surfaces: Smooth, glabrous. Color, upper and lower surfaces: Close to 146A.

Flower description:

*Flower appearance/arrangement.*—Single rotate flowers; terminal and axillary. Freely flowering habit with usually about six to eight flowers per lateral branch. Flowers face upright to outwardly.

*Flower longevity.*—Flowers last for about one day on the plant. Flowers not persistent.

*Natural flowering season.*—Typically during the months of July and August in Michigan.

*Flower diameter.*—About 9 cm.

*Flower length* (*height*).—About 5 cm.

*Flower bud.*—Length: About 2 cm. Diameter: About 1.4 cm. Shape: Ovate. Color: Close to 146C.

*Petals.*—Arrangement/quantity: Single whorl of five petals; petals imbricate. Length: About 5 cm. Width: About 3.8 cm. Shape: Obovate. Apex: Obtuse, rounded. Base: Attenuate. Margin: Entire; undulate. Texture, upper and lower surfaces: Smooth, glabrous. Color: When opening and fully opened, upper and lower surfaces: Towards the apex, close to 89A; mid-section, close to 93D; towards the base, close to 59A; venation, similar to petal color. Color of entire petal becoming closer to 89A with development.

*Petaloids.*—Arrangement/quantity: About 26 petaloids in several whorls; petaloids imbricate. Length: About 2.5 cm. Width: About 8 mm. Shape: Roughly spatulate. Apex: Obtuse, rounded. Base: Attenuate. Margin: Entire; undulate. Texture, upper and lower surfaces: Smooth, glabrous. Color: When opening and fully opened, upper and lower surfaces: Towards the apex, close to 89A; mid-section and towards the base, close to 93D; venation, similar to petal color. Color of entire petaloid becoming closer to 89A with development.

*Sepals.*—Appearance: Five sepals fused into a tubular calyx. Length: About 1.5 cm. Width: About 1.5 cm. Shape: Roughly ovate. Apex: Acute. Margin: Entire. Texture, upper and lower surfaces: Smooth, glabrous. Color, immature and mature, upper and lower surfaces: Close to 146B.

*Peduncles.*—Length: About 3 mm. Diameter: About 1.5 mm. Strength: Strong, flexible. Texture: Smooth, glabrous. Angle: About 45° to 60° from the stem. Color: Close to 146B.

*Reproductive organs.*—Androecium: Anther shape: Globular. Anther size: About 1 mm by 1 mm. Anther color: Close to 155D. Amount of pollen: Moderate. Pollen color: Close to 162A. Gynoecium: Pistil length: About 3 mm. Style length: About 3 cm. Style color: Close to 155D. Stigma appearance: Five, rounded. Stigma color: Close to 155D. Ovary color: Close to 157A.

*Seeds/fruits.*—Seed and fruit development have not been observed on plants of the new *Hibiscus* plant.

Garden performance: Plants of the new *Hibiscus* have been observed to have excellent garden performance and to tolerate rain, wind and temperatures ranging from about −10° C. to about 35° C.

Pathogen/pest resistance: Plants of the new *Hibiscus* have not been shown to be resistant to pathogens and pests common to *Hibiscus*.

It is claimed:

1. A new and distinct *Hibiscus* plant named 'Notwood3' as illustrated and described.

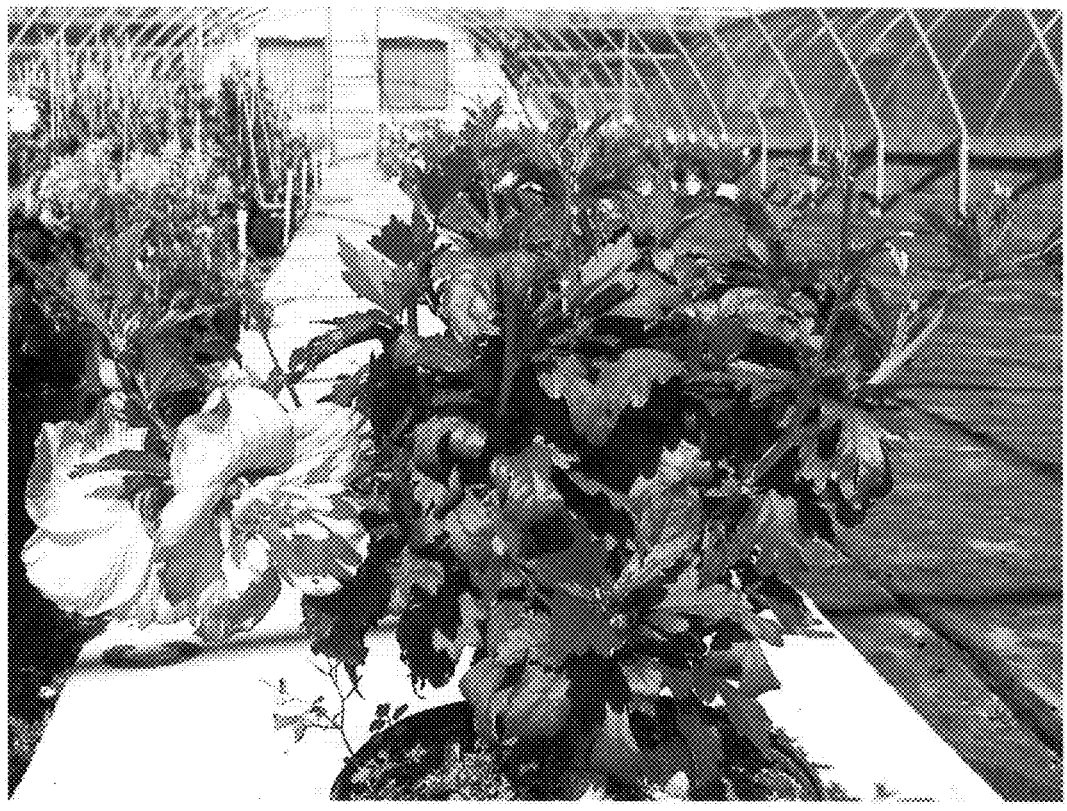

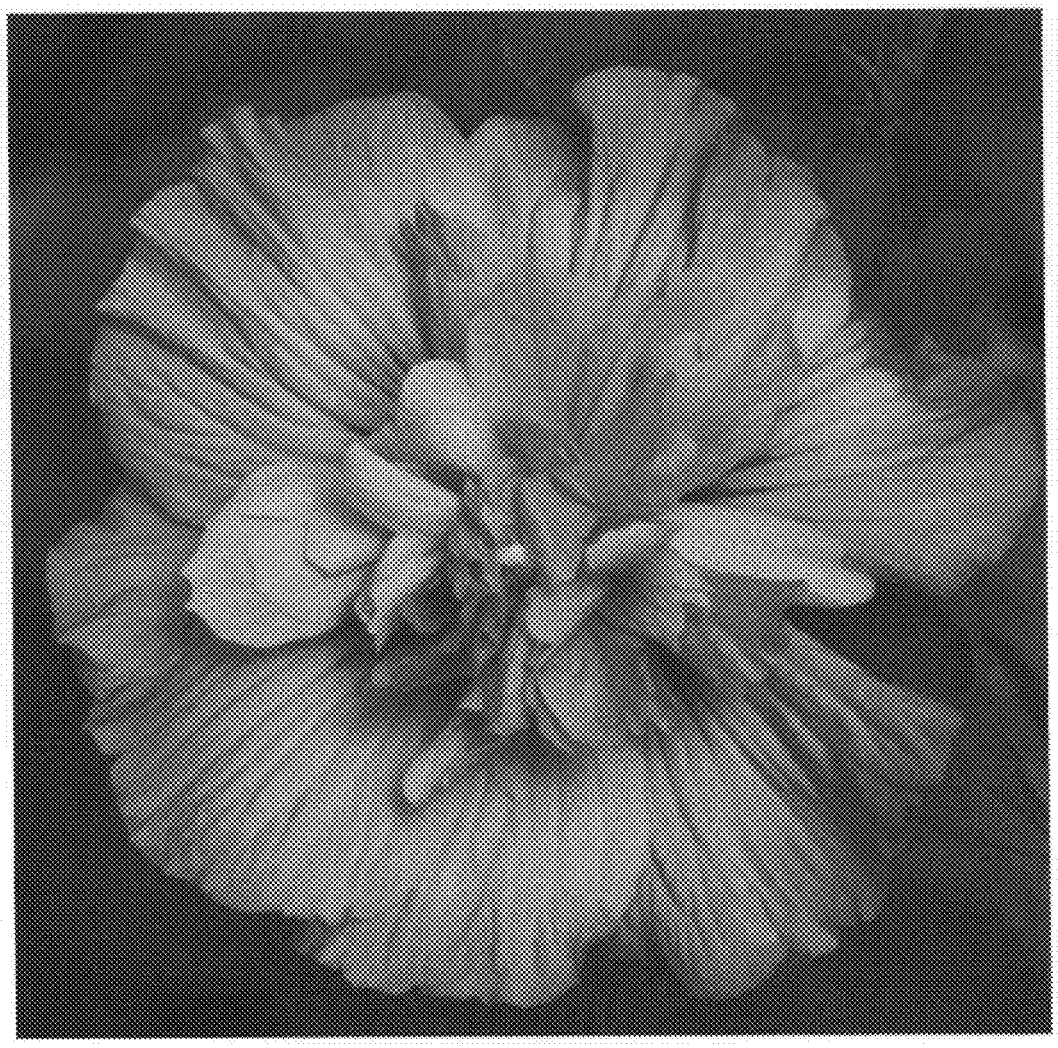

* * * * *